United States Patent [19]

Schmidt

[11] Patent Number: 4,673,760
[45] Date of Patent: Jun. 16, 1987

[54] PROCESS FOR THE PREPARATION OF VINYLCYCLOPROPANECARBOXYLIC ACID DERIVATIVES

[75] Inventor: Hans-Georg Schmidt, Niederkassel, Fed. Rep. of Germany

[73] Assignee: Dynamit Nobel AG, Troisdorf Bez Koeln, Fed. Rep. of Germany

[21] Appl. No.: 778,458

[22] Filed: Sep. 20, 1985

[30] Foreign Application Priority Data

Sep. 21, 1984 [DE] Fed. Rep. of Germany ....... 3434615

[51] Int. Cl.$^4$ .............................................. C07C 69/743
[52] U.S. Cl. ...................................... 560/124; 549/292
[58] Field of Search .......................................... 560/124

[56] References Cited

U.S. PATENT DOCUMENTS 3,723,469  3/1973  Martel ................................. 560/124
4,014,918  3/1977  Martel ................................. 560/124
4,342,704  8/1982  Hoffman .............................. 560/124
4,348,535  9/1982  Schmidt .............................. 560/124
4,492,800  1/1985  Maurer ................................ 560/124

Primary Examiner—Michael L. Shippen
Attorney, Agent, or Firm—Felfe & Lynch

[57] ABSTRACT

Disclosed is a process for preparing cis-trans isomer mixtures of 2,2-dimethyl-3($\beta,\beta$-dichlorovinyl)-cyclopropane-1-carboxylic acid esters, having a high cis/trans isomer ratio, wherein a 4,4-dimethyl-5-halogen-6-alkoxytetrahydro-pyrone or a 3,3-dimethyl-4-halogen-5-oxo-pentanic acid ester is reacted with dichlorophosphonic acid esters in the presence of alkali alcoholates or alkali hydrides or lithium alkyls.

Also disclosed are novel starting tetrahydropyrone compounds usable in the above process, and a process for preparation of the novel compounds which includes reacting $\beta,\beta$-dimethyl-$\gamma,\delta$-dihalogen-$\delta$-valerolactones with alkali alcoholates at reaction temperatures between $-10°$ and $+50°$ C.

5 Claims, No Drawings

PROCESS FOR THE PREPARATION OF VINYLCYCLOPROPANECARBOXYLIC ACID DERIVATIVES

BACKGROUND OF THE INVENTION

The subject matter of the present invention is a new process for the preparation of derivatives of vinylcyclopropanecarboxylic acid as well as new derivatives of tetrahydro-alpha-pyrone which are to be used as starting products in this process. Additional subject matter is a process for the preparation of these new derivatives of tetrahydro-alpha-pyrone.

The vinylcyclopropanecarboxylic acid derivatives of formula I below are important intermediates for the production of insecticides in the pyrethroid class. The potency of these pyrethroids depends on, among other things, the stereochemical configuration of the active molecule. Thus, for example, the cis form of cypermethrin is more effective than the trans form. The syntheses of cypermethrin starts out from 2,2-dimethyl-3-($\beta,\beta$-dichlorovinyl)-cyclopropane-1-carboxylic acid esters, which will be referred to hereinafter as cyclopropanecarboxylic acid esters, for the sake of simplicity (Synthetic Pyrethroids, ACS Symposium Series 42, p. 45). In European Patent B1 0 003 683 there is described a method of preparation, the purpose of which is the synthesis of the cis form of the above-mentioned cyclopropanecarboxylic acid ester. This method is here outlined briefly:

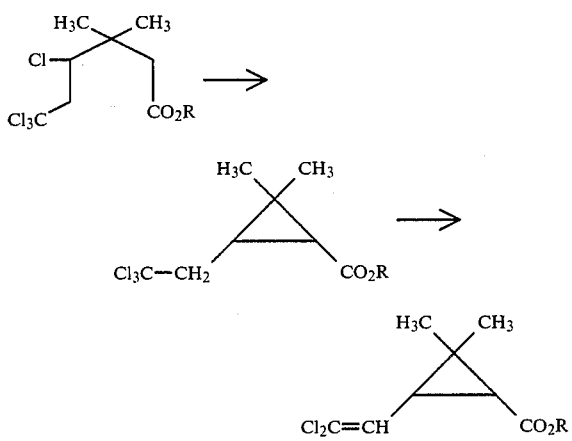

The disadvantage of this process is that the reaction to the cis form requires very special solvent mixtures, and that the preparation of the starting product can be accomplished only with great technical difficulty.

The problem therefore existed of finding a process for the preparation of the cyclopropane acid ester of formula I from easily obtained starting products different from those used heretofore, and which resulted in a very high content of cis isomers.

THE INVENTION

As the solution to this problem, a process has been found for the preparation of 2,2-dimethyl-3-($\beta,\beta$-dichlorovinyl)-cyclopropane-1-carboxylic acid esters, wherein a pentanoic acid ester of formula II

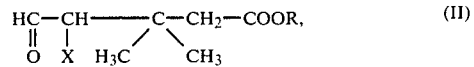

in which X represents chlorine or bromine and R, represents a group with 1–6 carbon atoms a 4,4-dimethyl-5-halogen-6-alkoxy-tetrahydropyrone of formula III

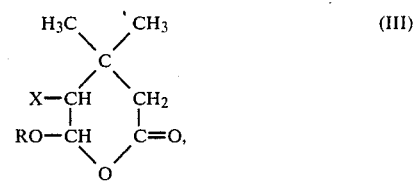

in which X and R have the meaning given above, or a lactone of the formula IV

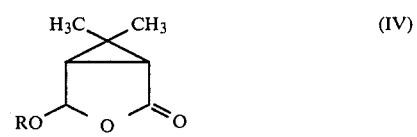

in which R and X have the meaning above is reacted with a basic compound in the presence of a dichlorophosphonic acid ester of the formula

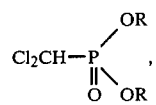

in which R has the meaning given above.

In the application of the new process, a cis-trans isomer mixture is obtained of the compound of formula I:

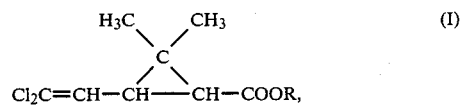

in which R represents a $C_1$ to $C_6$ alkyl moiety, and which contains more than 50% of the cis isomer.

The starting products for the new process are easily available compounds. The pentanic acid esters of formula II

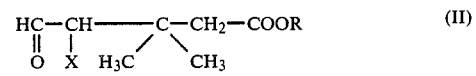

($R = C_1$ to $C_6$ alkyl, $X = Cl$ or Br) which are also referred to as 3,3-dimethyl-4-halogen-5-oxopentanic acid esters, are already-known compounds. They are prepared by the simple reaction of $\beta,\beta$-dimethyl-$\gamma,\delta$-dihalogen-$\delta$-valerolactones with alcohols. This process is described in German published application No. P 34 16 414.6.

The 4,4-dimethyl-5-halogen-6-alkoxytetrahydropyrones of the following formula:

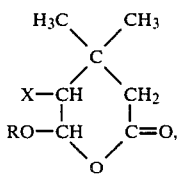

wherein R and X have the meaning given above, which can also be called β,β-dimethyl-γ-halogen-δ-alkoxy-δ-valerolactones, are new compounds. They too are prepared from the β-β-dimethyl-γ-δ-dihalogen-δ-valerolactones of formula IV:

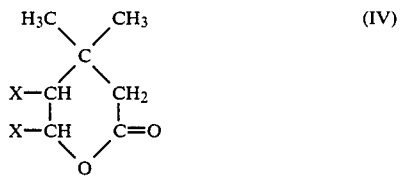

(X=Cl or Br) by transposition with alkali alcoholates or alcohols. The alcoholates or alcohols are used preferably in a stoichiometric ratio to the valerolactones, a slight excess of 1.1 to 1.2:1 being entirely possible.

The alcoholate moiety of the alcoholate used in this reaction can have up to 6 carbon atoms. Preferably the sodium and potassium alcoholates are used, such as for example the sodium and potassium methylates and ethylates. The alcohols used in this process also can have up to 6 carbon atoms.

The preparation of these new compounds is performed in the temperature range between −10° and +50° C. For a thorough mixing of the reactants it is recommendable to operate in an aprotic solvent. Examples of such solvents are: aliphatic and aromatic hydrocarbons which are liquid at room temperature, ethers such as tetrahydrofuran, or amines such as triethylamine. If alcohols are used instead of alcoholates a basic solvent is added, for example triethylamine. Preferably the process is conducted at atmospheric pressure.

For the process according to the invention for the preparation of the cyclopropanecarboxylic acid esters of formula I, both alkali alcoholates and alkali hydrides as well as lithium alkyls can be used as basic compounds. The amounts to be used are in each case 1 to 5 molar equivalents, preferably 2 to 2.5 molar equivalents of basic compounds, with respect to the input starting product. The compounds of formula III exists as a cis-trans-mixture with regard for the substituents X and OR. Such a cis-trans-mixture is preferably used as starting material for the formation of compounds of the formula I.

Suitably lithium alkyls are those whose alkyl group contains 1 to 8 carbon atoms, such as butyl lithium, for example. Examples of suitable alkali hydrides are sodium or potassium hydride. The preferred basic compounds are sodium or potassium alcoholates, in which the alcohol moiety can have 1 to 6 carbon atoms, preferably 1 to 4 carbon atoms.

The chlorophosphoric acid esters are used in amounts of 1 to 8 molar equivalents, with respect to the starting compounds. If no solvent is used, then it is recommended to use the phosphonic acid ester at least in a fivefold molar excess, in order to assure easy stirring of the reaction mixture. Preferably the process is conducted at atmospheric pressure.

Regardless of which starting products are used for the process of preparing the cyclopropanecarboxylic acid esters of formula I, the reaction temperature can be selected within the range of −50° C. to +100° C. It is surprising that even in the upper temperature range little or no isomerization occurs, or any direct steering toward the thermodynamically more stable trans isomers of general formula I. For the attainment of better stirrability, the reaction is performed in a solvent which is inert under the conditions of the reaction. Such solvents are, for example, ethers such as tetrahydrofuran, 1,4-dioxane, and aromatic hydrocarbons such as benzene, toluene and chlorobenzene; aliphatic hydrocarbons, which can be straight-chained, branched or cyclical, and nitriles, such as acetonitrile.

Examples

EXAMPLE 1

To a mixture of 4.0 g of 5-oxo-4-bromo-3,3-dimethylpentanic acid methyl ester, 3.4 g of dichloromethanephosphonic acid dimethyl ester, and 80 ml of the solvents named in Table 1, at 0° C. 2 molar equivalents of the alcoholates named in Table 1 are added gradually with stirring. Then stirring is continued for two hours at 20° C. Then 100 ml of ice water is added and the organic phase is separated from the aqueous phase. After drying the organic phase the solvent is withdrawn and the residue is tested by gas chromatography and NMR spectroscopy, and identified as 2,2-dimethyl-3(β,β-dichlorovinyl)-cyclopropane-1-carboxylic acid methyl ester. The cis-trans ratio in relation to the solvent is listed in Table 1.

TABLE 1

| Test | Solvent | Alcoholate | Crude yield | Cis:trans ratio |
|---|---|---|---|---|
| (a) | toluene | NaOCH$_3$ | 85% | 88:12 |
| (b) | 1,4-dioxane | NaOCH$_3$ | 80% | 87:13 |
| (c) | acetonitrile | NaOCH$_3$ | 83% | 85:15 |
| (d) | toluene | K-tert.-butylate | 79% | 90:10 |

EXAMPLE 2

To a mixture of 10.0 g of 5-oxo-4-chloro-3,3-dimethylpentanoic acid methyl ester, 21.0 g of dichloromethanephosphonic acid dimethyl ester and 20 ml of toluene, 3.0 g of NaOCH$_3$ is added gradually with stirring at 0° C. One hour later another 3.0 g of NaOCH$_3$ is added. After another three hours of stirring at 10° to 20° C., the mixture is worked up as described in Example 1. 6.7 g of 2,2-dimethyl-3(β,β-dichlorovinyl)-cyclopropane-1-carboxylic acid methyl ester is obtained. The cis-to-trans isomer ratio is 75:25.

EXAMPLE 3

To a mixture of 4.0 g of 5-oxo-4-bromo-3,3-dimethylpentanoic acid methyl ester, 4.1 g of dichloromethanephosphonic acid diethyl ester and 56 ml of toluene, 2.1 g of NaOCH$_3$ is added gradually at 0° C. After an hour of stirring another 2.1 g of NaOCH$_3$ is gradually added. After two more hours of stirring at 10° to 20° C., the mixture is worked up as in Example 1. 2.6 g is obtained of a mixture of 2,2-dimethyl-3(β,β-dichlorovinyl)-cyclopropanecarboxylic acid methyl ester and 2,2-dimethyl-3-(β,β-dichlorovinyl)-cyclopropanecarboxylic acid ethyl ester. The cis-to-trans isomer ratio of both esters is about 95:5.

EXAMPLE 4

To a mixture of 5.0 g of 4,4-dimethyl-5-bromo-6-methoxy-tetrahydro-alpha-pyrone, 4.5 g of dichloromethanephosphonic acid dimethyl ester and 70 ml of toluene, 2.4 g of NaOCH₃ is added gradually at 5° C. After one hour of stirring another 2.4 g of NaOCH₃ is added gradually, and then stirred for two hours at 10° to 20° C. Then the mixture is worked up as in Example 1. 3.3 g is obtained of 2,2-dimethyl-3(β,β-dichlorovinyl)-cyclopropanecarboxylic acid methyl ester is obtained. The cis-to-trans isomer ratio amounts to 97:3.

EXAMPLE 5

10 g of 4,4-dimethyl-5,6-dichlorotetrahydro-alpha-pyrone is dissolved in 30 g of triethylamine, and to this mixture 2.7 g of NaOCH₃ is added gradually, with stirring, at 20° C. Then the mixture is stirred for four hours at 20° C. and the solid is filtered out. The resulting filtrate is distilled. At 100° to 110° C. and 0.2 Torr, 7.1 g of 4,4-dimethyl-5-chloro-6-methoxy-tetrahydro-alpha-pyrone is distilled in the form of a cis-trans isomer mixture (cis-to-trans ratio approximately 20:80).

H-NMR spectrum (90 MHz, CDCl₃) δ ppm: 1.12 (3H); 1.15 (3H); 1.19 (3H)*; 1.22 (3H)*; 2.47 (2H); 2.68 (2H)*; 3.60 (3H); 3.63 (3H)*; 3.78 (1H); 3.98 (1H)*; 5.17 (1H); 5.31 (1H)*.
The signals marked * are associated with the cis isomer.

EXAMPLE 6

Analogously to Example 5, the 4,4-dimethyl-5-bromo-6-methoxytetrahydro-alpha-pyrone is prepared from 4,4-dimethyl-5,6-dibromotetrahydro-alpha-pyrone. Boiling point: 90° to 95° C. at 0.3 Torr. Cis-to-trans isomer ratio approximately 10:90.

H-NMR spectrum (30 MHz, CCl₄) δ ppm=1.25 (6H); 2.60 (2H); 3.65 (3H); 4.0 (1H); 5.35 (1H).

It will be understood that the specification and examples are illustrative but not limitative of the present invention and that other embodiments within the spirit and scope of the invention will suggest themselves to those skilled in the art.

EXAMPLE 7

To a mixture of 600 g triethylamine and 32,8 g methanol a mixture of 200 g 4,4-dimethyl-5,6-dichloro-tetrahydro-α-pyrone and 9 g toluene is added gradually with stirring within 2 h at a temperature of 20° C. Triethylamine-hydrochloride is formed. The salt is seperated by filtration and the organic liquid is distilled. 175 g 4,4-dimethyl-5-chloro-6-methoxy-tetrahydro-α-pyrone are obtained.

What is claimed is:

1. A process for the preparation of cis-trans isomer mixtures of 2,2-dimethyl-3(β,β-dichlorovinyl)-cyclopropane-1-carboxylic acid esters of formula I, which contain more than 50% of the cis isomer,

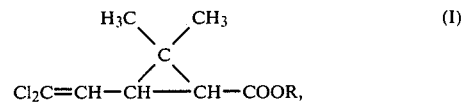

wherein R is an alkyl moiety of 1 to 6 carbon atoms, characterized in that (a) a pentanoic acid ester of formula II

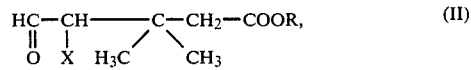

in which X is chlorine or bromine and R has the meaning given above, or (b) a 4,4-dimethyl-5-halogen-6-alkoxy-tetrahydropyrone of formula III

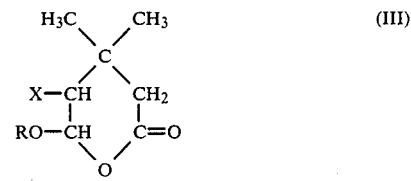

in which X and R have the meaning given above, or (c) a lactone of formula IV

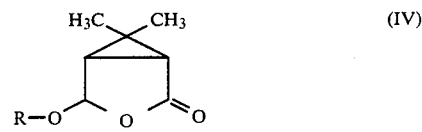

in which X and R have the meaning above, is reacted with a basic compound in the presence of a dichlorophosphonic acid ester of the formula

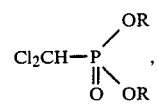

in which R has the meaning given above.

2. The process of claim 1 wherein the basic compound is sodium or potassium alcoholate.

3. The process of claim 1 wherein the basic compound is sodium or potassium hydride.

4. The process of claim 1 wherein the basic compound is lithium alkyl.

5. The process of claim 1 wherein the reaction is performed in a solvent.

* * * * *